(12) United States Patent
Komann et al.

(10) Patent No.: US 11,464,705 B2
(45) Date of Patent: Oct. 11, 2022

(54) HOLDING STRUCTURE FOR CONCURRENTLY HOLDING A PLURALITY OF CONTAINERS FOR SUBSTANCES FOR PHARMACEUTICAL, MEDICAL OR COSMETIC APPLICATIONS, TRANSPORT STRUCTURE AND TRANSPORT OR PACKAGING CONTAINER COMPRISING THE SAME

(71) Applicant: SCHOTT Schweiz AG, St. Gallen (CH)

(72) Inventors: Christian Komann, Speicher (CH); Levent Kusogullari, Winterthur (CH); Arne Kloke, St. Gallen (CH)

(73) Assignee: Schott Schweiz AG, St. Gallen (CH)

( * ) Notice: Subject to any disclaimer, the term of this patent is extended or adjusted under 35 U.S.C. 154(b) by 0 days.

(21) Appl. No.: 16/446,208

(22) Filed: Jun. 19, 2019

(65) Prior Publication Data

US 2019/0298610 A1    Oct. 3, 2019

Related U.S. Application Data

(63) Continuation of application No. PCT/EP2017/077761, filed on Oct. 30, 2017.

(30) Foreign Application Priority Data

Dec. 21, 2016    (DE) .................... 20 2016 107 209.3

(51) Int. Cl.
*A61J 1/16* (2006.01)
*A61M 5/00* (2006.01)
(Continued)

(52) U.S. Cl.
CPC ................ *A61J 1/16* (2013.01); *A61M 5/008* (2013.01); *A61B 50/33* (2016.02); *A61M 5/002* (2013.01); *B01L 9/06* (2013.01)

(58) Field of Classification Search
CPC . A61B 50/33; A61J 1/16; A61M 5/00; A61M 5/002; A61M 5/008; B01L 9/06;
(Continued)

(56) References Cited

U.S. PATENT DOCUMENTS 3,115,266 A * 12/1963 Poupitch ............ B65D 71/0003
206/203
3,416,694 A * 12/1968 Bebb ...................... B65D 1/243
220/518
(Continued)

FOREIGN PATENT DOCUMENTS

CN    101104453 A    1/2008
CN    102837868 A    12/2012
(Continued)

OTHER PUBLICATIONS

International Search Report and Written Opinion of the International Search Authority, including an English translation thereof, dated Jan. 10, 2018 for International Application No. PCT/EP2017/077761 (16 pages).
(Continued)

*Primary Examiner* — Bryon P Gehman
(74) *Attorney, Agent, or Firm* — Taylor IP, P.C.

(57) ABSTRACT

A holding structure for concurrently holding a plurality of containers for substances for pharmaceutical, medical or cosmetic applications includes a plurality of receptacles for receiving the containers therein at least in sections. The receptacles each have an open upper end for inserting the containers into the receptacles and a bottom end having a holding portion for limiting an axial movement of the containers in the receptacles. Guide portions are provided for guiding the containers as they are inserted into the receptacles. The guide portions are formed as guiding ribs extending in the longitudinal direction of the receptacles.
(Continued)

Lead-in bevels are formed at upper ends of the guiding ribs which are inclined relative to the guiding ribs.

20 Claims, 10 Drawing Sheets

(51) Int. Cl.
*A61B 50/33* (2016.01)
*B01L 9/06* (2006.01)

(58) Field of Classification Search
CPC .......... B65D 1/36; B65D 21/00; B65D 21/02; B65D 71/00; B65D 71/42; B65D 71/52; B65D 81/26; B65D 1/34; B65D 85/30
USPC .......................................... 206/203, 557–565
See application file for complete search history.

(56) References Cited

U.S. PATENT DOCUMENTS

| | | | |
|---|---|---|---|
| 4,113,087 A * | 9/1978 | Morcom | B29C 45/2624 |
| | | | 206/203 |
| 5,547,082 A * | 8/1996 | Royer | H05K 13/0084 |
| | | | 206/564 |
| 5,913,424 A * | 6/1999 | Kelly | B65D 21/0209 |
| | | | 206/509 |
| 5,961,086 A | 10/1999 | Moore et al. | |
| 8,118,167 B2 | 2/2012 | Togashi et al. | |
| 9,475,602 B2 * | 10/2016 | Apps | B65D 71/0003 |
| 9,522,752 B2 | 12/2016 | Wissner et al. | |
| 9,598,195 B2 | 3/2017 | Deutschle et al. | |
| 9,636,680 B2 | 5/2017 | Fattinger et al. | |
| 10,064,786 B2 * | 9/2018 | Tsukiji | A61M 5/002 |
| 10,124,928 B2 * | 11/2018 | Wissner | A61J 1/16 |
| 10,207,832 B2 * | 2/2019 | Narvekar | A61M 5/008 |
| 2005/0133386 A1 | 6/2005 | Wong | |
| 2007/0110928 A1 * | 5/2007 | Bried | B65D 1/22 |
| | | | 264/299 |
| 2009/0100802 A1 | 4/2009 | Bush et al. | |
| 2015/0114871 A1 | 4/2015 | Fitzpatrick et al. | |
| 2015/0272827 A1 | 10/2015 | Tsukiji | |
| 2018/0235838 A1 * | 8/2018 | Kawamura | A61J 1/16 |

FOREIGN PATENT DOCUMENTS

| | | |
|---|---|---|
| CN | 103359348 A | 10/2013 |
| DE | 297 00 878 U1 | 3/1997 |
| EP | 2 448 541 B1 | 7/2013 |
| EP | 2 740 537 A1 | 6/2014 |
| EP | 2 848 882 A1 | 3/2015 |
| EP | 2 868 593 A1 | 5/2015 |
| WO | 2014/072019 A2 | 5/2014 |
| WO | 2016/135051 A1 | 9/2016 |
| WO | 2016/166765 A1 | 10/2016 |

OTHER PUBLICATIONS

Translation of the Written Opinion of the International Searching Authority dated Jan. 10, 2018 for International Application No. PCT/EP2017/077761 (6 pages).

English translation of Chinese Office Action dated Jan. 28, 2021 for Chinese Application No. 201780079159.9 (10 pages).

"Questions and Answers on Plastic Molding Technology", Li Guozhi, et al., Printing Industry Press, pp. 121-122, Jun. 2012 (2 pages).

* cited by examiner

HOLDING STRUCTURE FOR CONCURRENTLY HOLDING A PLURALITY OF CONTAINERS FOR SUBSTANCES FOR PHARMACEUTICAL, MEDICAL OR COSMETIC APPLICATIONS, TRANSPORT STRUCTURE AND TRANSPORT OR PACKAGING CONTAINER COMPRISING THE SAME

CROSS REFERENCE TO RELATED APPLICATIONS

This is a continuation of PCT application No. PCT/EP2017/077761, entitled "HOLDING STRUCTURE FOR CONCURRENTLY HOLDING A PLURALITY OF CONTAINERS FOR SUBSTANCES FOR PHARMACEUTICAL, MEDICAL OR COSMETIC APPLICATIONS, TRANSPORT STRUCTURE AND TRANSPORT OR PACKAGING CONTAINER COMPRISING THE SAME", filed Oct. 30, 2017, which is incorporated herein by reference.

BACKGROUND OF THE INVENTION

1. Field of the Invention

The present disclosure generally relates to the processing of containers for substances for pharmaceutical, medical or also cosmetic applications, and in particular to a holding structure for concurrently holding a plurality of containers for substances for pharmaceutical, medical or also cosmetic applications as well as to a transport structure or a transport or packaging container with such a holding structure and containers held thereon.

2. Description of the Related Art

Medicine containers, such as vials, ampoules or cartridges, are used on a large scale as containers for the storage and storing of medical, pharmaceutical or cosmetic preparations with administration in liquid form, especially in pre-dosed quantities. These generally have a cylindrical shape, can be made of plastic material or glass and are available in large quantities at low cost. Lyophilization processes are increasingly used after filling to fill containers as economically as possible under sterile conditions and for long-term storage. For this purpose, the containers must be unpacked under sterile conditions at the filler, e.g. a pharmaceutical company, and then further processed.

Chinese Patent Application CN 103359348-A discloses a holding structure in the form of a tray having a bottom on which a plurality of vertical positioning pins are provided between which the containers can be accommodated without mutual contact. The holding structure is formed by injection molding of a plastic material. At the same time, the vertical positioning pins act as guide portions for inserting the containers into the receptacles formed by the positioning pins.

International Patent Application WO 2016/135051 A1 discloses a further holding structure which is designed as a so-called nest and can be accommodated in a tub-shaped transport or packaging container (also referred to as tub). On the underside of the holding structure a plurality of receptacles are formed, the bottoms of which are connected to one another, with vertical positioning pins projecting from the bottoms, between which the containers can be accommodated without mutual contact. Here, the vertical positioning pins act as guide portions for inserting the containers into the receptacles formed by the positioning pins.

Further holding structures are disclosed in European Patent Applications EP 2868593A1, EP 2848882 A1, and EP2740537 A1 and International Patent Application WO 2014/072019 A2.

European Patent Application EP 2 448 541 B1 discloses a further holding structure having tubular receptacles formed by side walls projecting perpendicular to an upper side of the holding structure.

The insertion of the containers from above into the receptacles of the holding structures always requires a very precise pre-positioning of the containers relative to the receptacles, which is complex.

Due to the production of the aforementioned holding structures by an injection molding or deep-drawing process from plastic material, the geometry of the receptacles varies to a certain extent, for example due to warpage, demolding bevels, roundness, concentricity, etc. These variations lead to an increase in the clearance between the containers and the holding structure, which results in greater freedom of movement for the containers in the receptacles, but also in more particles due to material abrasion and in a reduction in the packing density that can be achieved. A subsequent post-processing of the holding structure in the tool is very complex here, so that certain geometrical variations cannot be avoided.

Due to the ejection process during injection molding of the holding structures, correspondingly large demolding bevels need to be provided at pockets or receptacles of the holding structures shrinking on the cores of molds for injection molding, wherein the angle of inclination of the demolding bevels must be at least approx. 2°. Such large demolding bevels, however, result in a relatively inaccurate guidance, especially in the case of relatively long and slim containers such as cartridges, and result in a lower packing density.

German Utility Model DE 297 00 878 U1 discloses a bottle case in which bottles are accommodated between cylindrical guide pins with guiding ribs at their front edges. Rounded end faces are provided at the upper ends of the guide pins.

U.S. Patent Application Publication No. 2005/0133386 A1 discloses a bottle carrier in which the bottles to be held must be suspended from below. Guiding ribs and lead-in bevels in the sense of the present application are not disclosed.

U.S. Patent Application Publication No. 2015/0272827 A1 discloses a nest for vials. The vials are accommodated upside down in the receptacles of the nest. The receptacles are formed by circumferential guide pins, wherein the bottom of the receptacles is closed. Stepped guide portions are provided on the guide pins, on which the shoulders of the vials rest.

SUMMARY OF THE INVENTION

Exemplary embodiments disclosed herein provide an improved holding structure for concurrently holding a plurality of containers for substances for pharmaceutical, medical or cosmetic applications, which can be easily and cost-effectively manufactured and allows an easy and reliable insertion of the containers into the receptacles of the holding structure. Further embodiments of the present disclosure relate to transport structures or transport or packaging containers and a sterile packaging structure comprising such a holding structure.

In some exemplary embodiments, there is provided a holding structure for concurrently holding a plurality of containers for substances for pharmaceutical, medical or cosmetic applications, in particular a plurality of vials or cartridges, having a plurality of receptacles for receiving the containers therein at least in sections or completely, so that upper or bottom ends of the containers protrude axially from the receptacles or do not do so. The receptacles each have an open upper end for inserting the containers into the receptacles and a bottom end having a holding portion. The holding portion serves to limit an axial movement of the containers in the receptacles, i.e. to retain the containers axially secured in the receptacles. In addition, guide portions are provided to guide the containers when they are inserted into the receptacles.

According to the present disclosure the guide portions are formed as guiding ribs extending in the longitudinal direction of the receptacles. Lead-in bevels are formed at the upper ends of the guiding ribs which are inclined relative to the guiding ribs.

The guiding ribs are relatively narrow when viewed transverse to the longitudinal direction of the receptacles. According to the present disclosure, this enables the containers to be held by the guiding ribs of the receptacles with a relatively close fit, but that they can slide easily into the receptacles. At the same time, the lead-in bevels at the upper ends of the guiding ribs effectively support the insertion of the containers into the receptacles. The lead-in bevels act as a kind of capturing funnel to capture the ends of the containers when they are inserted from vertically above the holding structure and guide them in the direction towards the guiding ribs. Thus, according to the present disclosure the containers have to be pre-positioned relative to the receptacles less precisely, which reduces the effort for handling the containers, but these can still be reliably inserted into the receptacles. To insert the containers into the receptacles, a coarse pre-positioning of the containers vertically above the receptacles may be sufficient. The containers are then lowered perpendicularly to the holding structure into the receptacles, whereby the containers even can be simply dropped due to the capturing effect described above if the guiding ribs and lead-in bevels are suitably designed, in order to then be guided into the receptacles.

Generally, the lead-in bevels may begin directly at the upper end of the receptacles to reduce the effective diameter of the receptacles to the diameter between the guiding ribs. In general, however, the lead-in bevels may also begin only at a certain distance from the upper ends of the receptacles, so that the opening width of the receptacles at their upper ends can then be maximum to efficiently capture the containers when they are inserted into the receptacles.

Generally, the lead-in bevels may also be concave, but may be planar, inclined surfaces at the upper ends of the guiding ribs, which then merge into the guiding ribs by changing their angle of inclination.

It may be sufficient if the guiding ribs protrude radially inwards from side walls or side wall portions of the receptacles only to a relatively small extent, for example by a distance that can be of the order of one millimeter or less only. According to the present disclosure, this enables a very high packing density of the holding structure. The guiding ribs or at least their front edges may be designed as planar, inclined surfaces.

According to the present disclosure, the angle of inclination of the guiding ribs relative to the central axis of the receptacles may be negligible in principle or it is of the order of one degree or less in order to facilitate the demolding of the holding structure from an injection mold during manufacture by injection molding. The very small or even negligibly small demolding bevels on the surfaces of the guiding ribs that are relevant for the guidance of the containers result in a very precise positioning and guidance of the containers in the receptacles and thus a precisely adjustable restriction of the freedom of movement of the containers in the receptacles or a considerable reduction of tilting of the containers accommodated in the receptacles. The restriction of the freedom of movement of the containers in the receptacles reduces both the movements of the containers relative to the holding structure and the impact speeds and thus the forces in the event of collision of the containers with the side walls or side wall portions of the receptacles during transport. These reduced normal forces and friction paths then result in smaller friction forces and lower material abrasion (formation of particles) when the containers are accommodated in the receptacles, but also when they are inserted into the receptacles. Furthermore, the very precise guidance of the containers, which is possible according to the present disclosure, also enables very precise removal of the containers from the receptacles, for example by lifting the containers by pre-positioned grippers. Such guiding ribs also allow geometrical deviations, such as warpage, roundness, concentricity, etc., which are caused by the injection molding process for producing the holding structure, to be precisely adapted and adjusted subsequently.

The very precise positioning and guidance of the containers in the receptacles according to the present disclosure makes it possible to increase the packing density, especially in the case of long, thin or slim containers, because a glass-to-glass contact of containers becomes less likely with increasing restriction on the freedom of movement. The gauge can thus be selected more narrowly.

The necessary guide length can also be reduced by greatly reducing the freedom of movement of the containers in the receptacles. This is relevant, for example, for long, thin or slim containers, such as cartridges or syringe cylinders, especially with small formats, because these can often only be inserted up to the lower half into the receptacles. Due to the very precise positioning and guidance of the containers according to the present disclosure, it can nevertheless be reliably ensured that there is no glass-to-glass contact. Thus, according to the present disclosure also material can be saved.

In some embodiments, the lead-in bevels are inclined relative to the guiding ribs at an angle between 5° and 15°, such as between 10° and 15° and or between 12.5° and 14.5°. On the one hand, this enables an efficient capturing of the containers during insertion perpendicular to the plane of the holding structure and, on the other hand, a reliable insertion into the receptacles formed by the underneath guiding ribs. The transition region to the guiding ribs may be angled or curved.

According to some embodiments, the lead-in bevels are inclined at a greater angle of inclination to the central axis of the receptacles than the guiding ribs. Since the angle of inclination of the guiding ribs to the central axis of the receptacles is negligible or at least very small, particularly in the range of only about one degree, the angle of inclination of the guiding ribs essentially corresponds to the angle of inclination of the lead-in bevels.

According to some embodiments, the angle of inclination of the guiding ribs relative to the central axis of the receptacles is between 0° and 2°, such as between 0° and 1.5° or between 0.5° and 1.0°. Thus a support of the containers in the receptacles with a relatively close fit can be accomplished, wherein the containers may only rest on the planar or crowned front sides of the guiding ribs along linear regions.

According to some embodiments, the guiding ribs protrude radially inwards into the receptacles and are arranged distributed and at angular spacings from each other, such as at equal angular distances from each other, in particular at angular distances of 90 degrees or 45 degrees. It may be sufficient if the guiding ribs protrude only minimally into the receptacles radially inwards, for example by a maximum distance of about one millimeter.

According to some embodiments, the guiding ribs of a respective receptacle surround a circle or are distributed along such a circle whose diameter is smaller than a diameter of the receptacles formed by side walls, positioning pins, separation webs or the like, wherein the diameter of the afore-mentioned circle at the bottom ends of the guiding ribs corresponds to an outer diameter of the containers at their end. At least in the region of the bottom of the receptacles, the containers are then held with a close fit between the guiding ribs. In particular, the cylindrical side walls of the containers rest directly against the guiding ribs at the bottom ends of the receptacles. The containers can therefore be supported in this region essentially without radial play.

According to some embodiments, the receptacles are arranged distributed in several rows and columns, wherein inner receptacles of the holding structure, i.e. receptacles which are not arranged directly at the edge of the holding structure, are formed by positioning cylinders which extend in axial direction, wherein a plurality of guiding ribs are provided on side walls of the positioning cylinders. These positioning cylinders may basically represent the only lateral boundaries of the receptacles, i.e. be arranged in the middle between four adjacent receptacles. Here, the actual lateral support of the containers is provided by the guiding ribs.

According to some embodiments, the guiding ribs of diametrically opposite positioning cylinders of a respective receptacle are arranged in alignment, whereby the guiding ribs on the side walls of the positioning cylinders are offset from each other by 90°. This means that the containers are supported laterally by only four guiding ribs, so that frictional forces are minimized, for example when the containers are inserted into the receptacles.

According to some embodiments, the guiding ribs and the associated lead-in bevels have a relatively small extension in the circumferential direction of the receptacles, i.e. are designed as relatively narrow ribs. For example, the extension in the circumferential direction of the receptacles may be in the range of a few angular degrees, for example in the range from 1 angular degree to about 15 angular degrees, such as in the range from 1 angular degree to 8 angular degrees or in the range from 1 angular degree to 2 or 3 angular degrees.

According to some embodiments, the guiding ribs can definitely have a certain extension in the circumferential direction of the receptacles, i.e. they are not only designed as linear, very narrow ribs, because this results in lower surface pressures when the containers are accommodated, so that the local quantity of particles due to material abrasion at the guiding ribs is smaller, i.e. this is then less critical for optical inspection systems. Namely, a reduction of the surface pressure creates smaller mechanical loads on the surfaces (i.e. the softer plastic surfaces of the holding structure).

In order to produce a guide structure consisting of closely fitting ribs, the guiding ribs of the holding structure may be further processed after their production, in particular by injection molding from a plastic material, and optimally adapted to the geometry of the containers to be accommodated.

According to some embodiments, the positioning cylinders are connected to each other via separation webs, which are aligned along rows and columns. The separation webs mainly serve to reinforce the holding structure so that the positions of the positioning cylinders can be specified with even greater accuracy. The separation webs can also be used to prevent direct glass-to-glass contact between the containers in the receptacles. Additional ribs may be provided on the side surfaces of the separation webs, which also extend in the longitudinal direction of the receptacles and may also serve as additional lateral support for the containers in the receptacles.

Generally, the receptacles may also be hexagonal by a suitable arrangement of the positioning cylinders in a hexagonal arrangement.

According to some embodiments, the positioning cylinders are hollow cylindrical, which further increases the rigidity of the positioning cylinders and helps to save material. An upper side edge of the positioning cylinders may be rounded, so that a container can be captured and guided even more effectively into a receptacle when inserted from vertically above the holding structure.

According to some embodiments, outer receptacles of the holding structure, i.e. receptacles which are disposed directly at the edge of the holding structure, are formed by side walls which are circularly curved at least in sections and which extend perpendicularly to the upper side of the holding structure or in parallel with the central axis of the receptacles. The side walls are matched to the cylindrical side walls of the containers such that the distance between the receptacles and the edge of the holding structure can be minimized. Here, an upper edge of the side walls may be rounded, which further supports the vertical insertion of the containers into the receptacles from above the holding structure.

According to some embodiments, the holding portions at the bottom ends of the receptacles are designed as holding protrusions protruding radially inward, so that the ends of the containers can be supported directly on these holding protrusions. The holding protrusions are designed to be sufficiently stiff to withstand the standard axial forces. If further processing of the containers is envisaged while they are accommodated in the receptacles of the holding structure, the stiffness of these holding protrusions may be considerable, so that relatively high axial forces can also be exerted on the containers accommodated in the receptacles, for example when placing plugs via the filling openings of cartridges, while the cartridges are supported on the holding protrusions at the ends opposite the filling openings.

Here, the holding protrusions may each surround openings at the bottom ends of the receptacles, so that the ends of the containers, when accommodated in the receptacles of the holding structure, may in principle be accessible at least in portions from the underside of the receptacles, for example for further processing or handling.

According to some embodiments, the containers are generally cylindrical, in particular in the form of cartridges, wherein these have an upper end with a constricted neck portion and an adjoining shoulder portion which merges into a cylindrical side wall of the containers, the opening width of the aforementioned openings being matched to the external diameters of the upper ends of the containers in such a manner that the upper ends of the containers extend through these openings and that the shoulder portions of the containers are supported directly on the holding protrusions in order to limit the axial mobility of the containers inside the receptacles. This design is particularly suitable for holding cartridges upside-down in the holders of the holding structure. Here, the ejection openings of the cartridges may be closed by a stopper and sealed with a lid or closure, e.g. by a crimped-on metal lid that still allows access to a septum in the stopper (pre-crimped cartridge). The opening widths of the aforementioned openings at the bottom ends of the receptacles may be dimensioned such that the front end of the cartridge with the stopper and the crimped-on metal lid may extend completely through this opening, so that the cartridges are supported on the holding protrusions exclusively in the region of the shoulder portions. For this purpose, the opening may be circular, or corresponds to the profile of the cartridge at its front end.

According to some embodiments, an upper side of the holding structure is planar at least along the edge of the holding structure, the bottom ends of the receptacles being connected to each other by webs which jointly span a plane. This results in a high stiffness of the holding structure with low space and material requirements. All in all, the holding structure can be designed as a so-called nest for receiving the plurality of containers in it for nest-and-tub packaging concepts.

According to some embodiments, the length of the receptacles is matched to the length of the containers such that upper or bottom ends of the containers protrude from the receptacles and are therefore freely accessible from above the holding structure. This can be used for further processing or treatment of the containers while they are accommodated in the receptacles and held by the holding structure. For example, a nest may be temporarily held in a holding frame of a process station, e.g. at a pharmaceutical filling company, while the substance is filled into the containers held on the holding structure via the filling openings. Or plugs are pushed into the ends of the containers to close the containers while the containers are held by the holding structure. Or the ends protruding from the receptacles can be used to grip the containers and remove them from the receptacles.

According to some embodiments, the holding structure is formed in one piece by injection molding from a plastic material. The aforementioned inclined guiding ribs and/or lead-in bevels can effectively support the demolding of the holding structure from an injection mold.

In some embodiments, there is provided a transport structure for containers consisting of a combination of the holding structure as disclosed above and a plurality of containers for substances for pharmaceutical, medical or cosmetic applications held thereon. The containers are accommodated at least in portions in the receptacles of the holding structure and are held on the holding structure secured in axial direction as outlined above. For this purpose, the holding structure may be designed in particular as a so-called nest for holding vials, cartridges or similar pharmaceutical containers.

According to some embodiments, the holding structure is designed as a receiving member in which the plurality of the receptacles are formed as frustoconical receptacles in a regular arrangement so that the containers are directed with their upper ends towards the bottoms of the receptacles and can be accommodated in the receptacles of the receiving member while preventing direct contact of adjacent containers. The receiving member may serve as a holding tray for the containers (so-called tray) and may also be sealed directly for sterile transport and storage of the containers, for example by a sealing foil.

Here, the receptacles may be matched to the lengths of the containers in such a manner that the containers are accommodated completely in the receptacles, i.e. their ends do not protrude from the receptacles.

According to some embodiments, a support member is also provided to cover the bottoms of the containers accommodated in the receiving member, wherein the support member is formed by a base plate having a planar support surface facing the receptacles.

Such a receiving member may be formed in one piece, in particular by thermoforming a plastic material, in particular by deep-drawing a sheet-like plastic material. Here, the receiving member may be formed by deep drawing a thin foil or a thin foil plate with a material thickness of up to 2.0 mm, such as of up to 1.25 mm or of up to 1.0 mm.

Here, the support member may also be formed in one piece by thermoforming a plastic material, in particular by deep drawing from a plate-shaped plastic material. In particular, the support member may be formed by deep-drawing a thin foil or a thin foil plate with a material thickness of up to 2.0 mm, such as of up to 1.25 mm or of up to 1.0 mm.

In some embodiments, there is provided a transport structure for containers consisting of a combination of the holding structure as described above and a plurality of containers held thereon for substances for pharmaceutical, medical or cosmetic applications. The containers are accommodated in the receptacles and are axially secured to the holding structure.

In some embodiments, there is provided a transport or packaging container for a plurality of containers for substances for pharmaceutical, medical or cosmetic applications, the transport or packaging container being box-shaped. A holding structure, which is formed as outlined above as a so-called nest, is accommodated in the box-shaped transport or packaging container together with the containers held thereon, for holding the plurality of containers in the transport or packaging container.

The transport or packaging container may in particular be closed or sealed by a gas-permeable plastic film, in particular by a plastic film which is formed from a gas-permeable braid of plastic fibers and in particular is a TYVECK® film, in order to enable sterilization of the containers by the inflow of a gas through the gas-permeable plastic film.

For a sterile transport and storage, a sterile packaging structure may further be provided, comprising at least one transport structure as outlined above or at least one transport or packaging container as outlined above and with the containers accommodated therein. The at least one transport structure or the at least one transport or packaging container is accommodated in at least one sterile outer packaging bag and sterilely packed against the environment. Here, the at least one sterile outer packaging bag may comprise a gas-permeable portion which is formed in particular by a braid of plastic fibers, such as polypropylene fibers (PP).

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
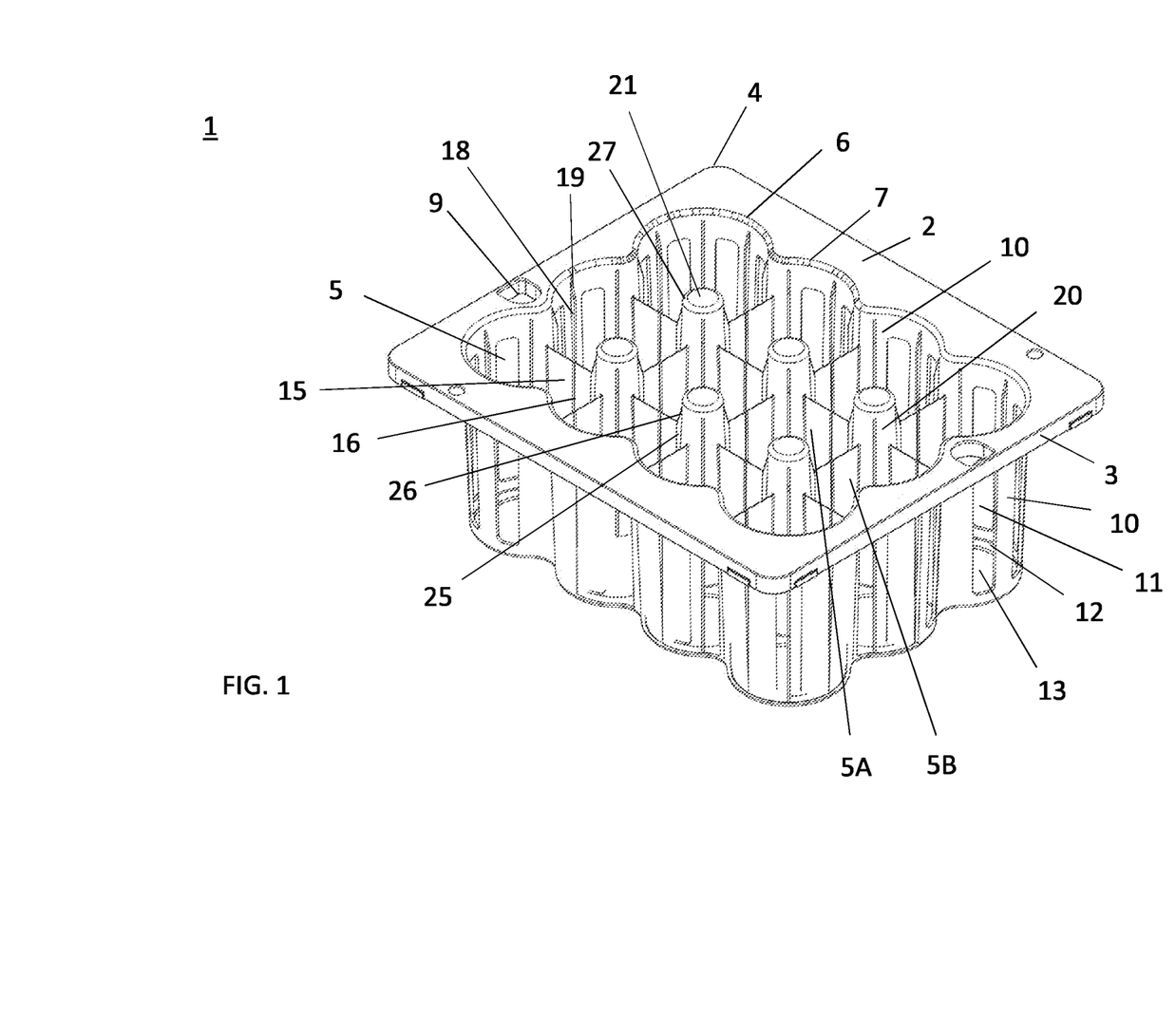
FIG. 1 illustrates a holding structure according to an exemplary embodiment of the present disclosure in a perspective view.
Figure 2:
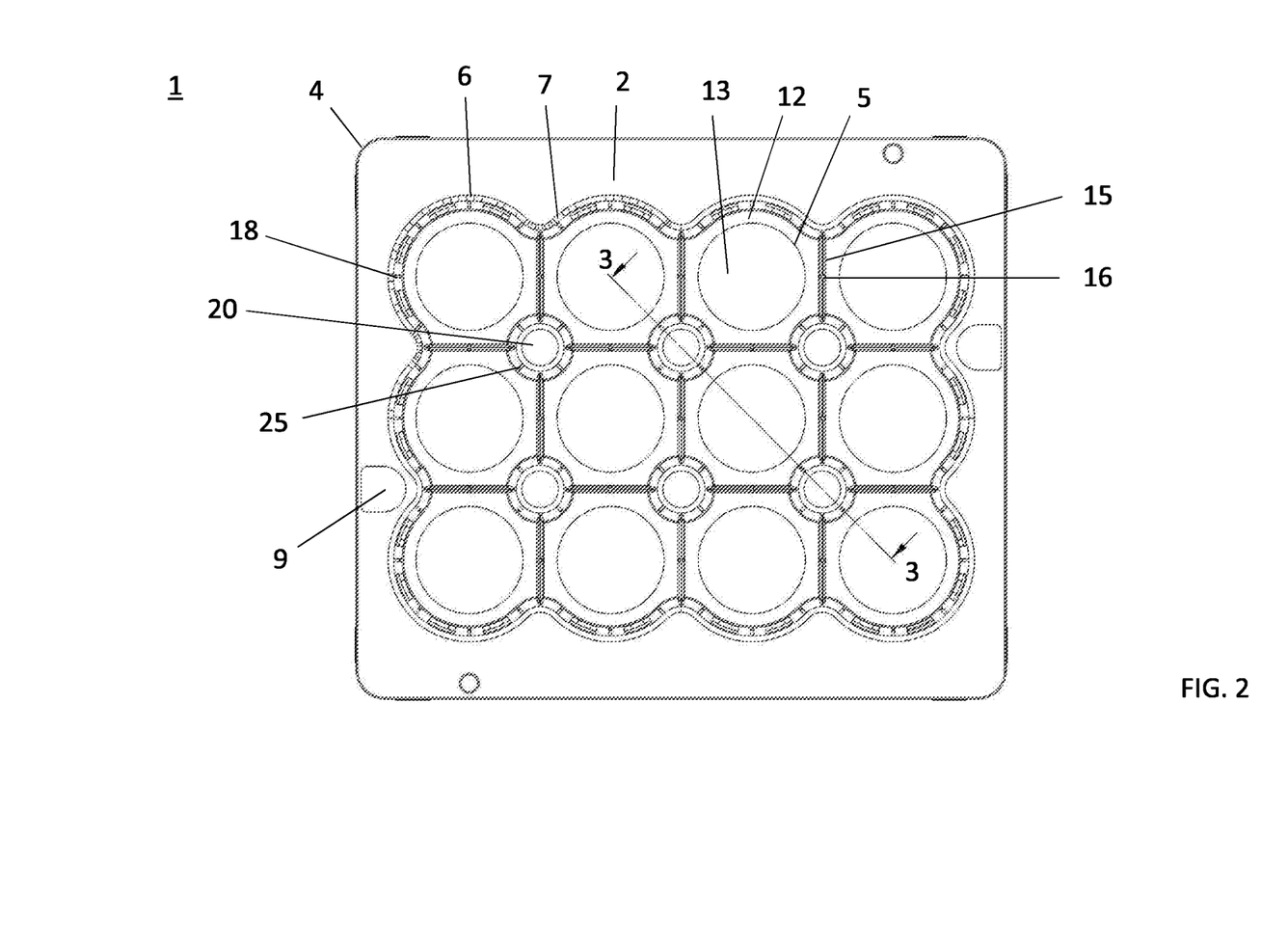
FIG. 2 illustrates the holding structure according to FIG. 1 in a plan view.

FIGS. 1 and 2 show a holding structure 1 provided according to an exemplary embodiment of the present disclosure in a perspective view and in a top view. The holding structure 1 comprises a plurality of receptacles 5 that are arranged in rows and columns extending perpendicularly to them and serve for accommodating pharmaceutical containers, in particular vials or cartridges. The receptacles 5 are separated from each other by vertical positioning cylinders 20, which are connected to each other by plate-shaped separation webs 15 and connected to side walls 10 that are circularly curved in sections. Along the edge of the holding structure 1, outer receptacles 5B are arranged, which are separated from each other by side walls 10 and separation webs 15. The remaining inner receptacles 5A are separated from each other exclusively by the separation webs 15.

Access openings 9 in the upper side 2, which are disposed offset to each other on two opposite sides of the holding structure 1, serve for gripping the holding structure 1.

The receptacles 5 extend perpendicularly to the upper side 2 and are delimited in axial direction at their bottom ends by bottom webs 12, which are connected to the side walls 10 and the bottom ends of the positioning cylinders 20 and together span a plane (see FIG. 6), which serves to further reinforce the receptacles. The bottom webs 12 enclose circular openings 13 at the bottom ends of the receptacles and are connected to each other. The upper ends 21 of the positioning cylinders 20 are flush with the upper side 2. The edge 6 of the upper side 2 and the upper ends 21 of the positioning cylinders 20 have rounded or beveled edges 7.

Longitudinal slots 11 are formed in the side walls 10 of the receptacles in order to save material and enable an optical inspection of the containers accommodated in the receptacles. The separation webs 10 are mainly used for further stiffening of the holding structure 1 and the positioning cylinders 20, but can also prevent direct contact between containers accommodated in adjacent receptacles 5.

On all side walls 10 and positioning cylinders 20, guiding ribs 18, 25 are provided, which protrude radially inwards into the receptacles 5, so that the side walls of the containers do not come into contact with the side walls 10 and positioning cylinders 20, but rest directly against the guiding ribs 18, 25 and are guided by them during insertion into the receptacles 5. The guiding ribs 18, 25 essentially extend over the entire length of the receptacles 5 in their longitudinal direction. As shown in FIG. 1, the guiding ribs 18, 25 start at a slight distance to the upper side 2 of the holding structure 1 and each extend down to the bottom of the receptacles 6. While it is shown in the figures that the guiding ribs 18, 25 do not have any interruptions in their longitudinal direction, these may basically also be formed with interruptions. The upper ends of the guiding ribs 18, 25 have lead-in bevels 19, 26 which are inclined at an acute angle relative to the guiding ribs 18, 25. In the embodiment shown, the guiding ribs 18, 25 are designed as planar lead-in bevels. The upper ends of the lead-in bevels 19, 26 merge into the side walls 10 or positioning cylinders 20.

Figure 3:
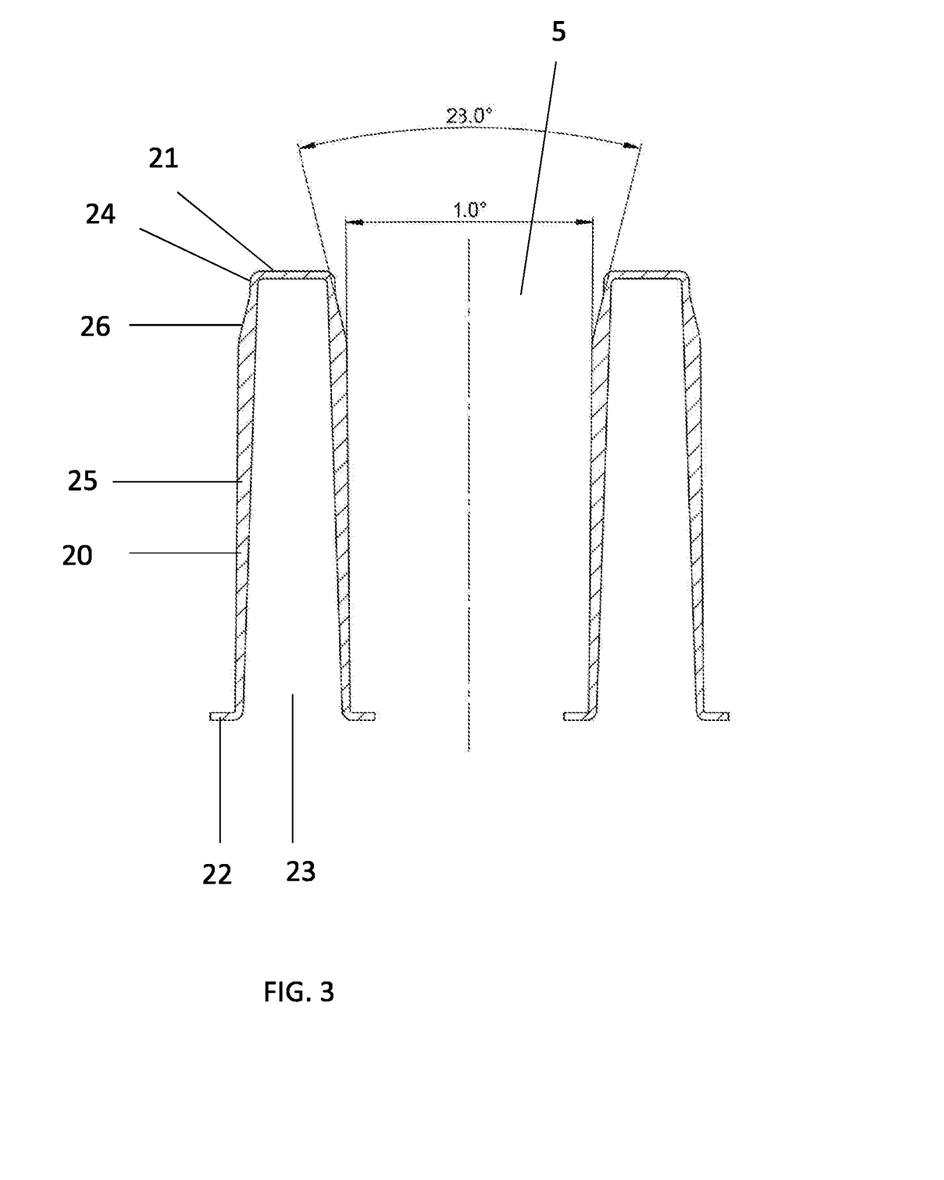
FIG. 3 illustrates a partial sectional view along line 3-3 in FIG. 2.

FIG. 3 shows a partial section along line 3-3 in FIG. 2. It can be seen that the positioning cylinders 20 are hollow and cylindrical, with the holding protrusions 22 projecting radially inwards into the receptacles 5 vertically from the bottom ends of the positioning cylinders 20. According to FIG. 3, the guiding ribs 25 are inclined at an angle of inclination of 0.5° relative to the central axis of the receptacles 5. This angle of inclination may also be negligible, but anyway it is very small; in some embodiments it is maximal 2°. When producing the holding structure by an injection molding process, the guiding ribs 18, 25 may serve as demolding bevels to assist in demolding from an injection mold. As shown in FIG. 3, the lead-in bevels 26 are inclined at an angle of 14° relative to the guiding ribs 25, which also applies to the corresponding angle of inclination of the lead-in bevels 19 relative to the guiding ribs 18 on the side walls 10 of the receptacles 5.

For radial support of the containers in the receptacles, several guiding ribs 18, 25 are arranged in each receptacle 5 spaced apart from each other, preferably at equal angular distances from each other on the side walls 10 and at equal angular distances from each other on the outer sides of the positioning cylinders 20.

Figure 4A:
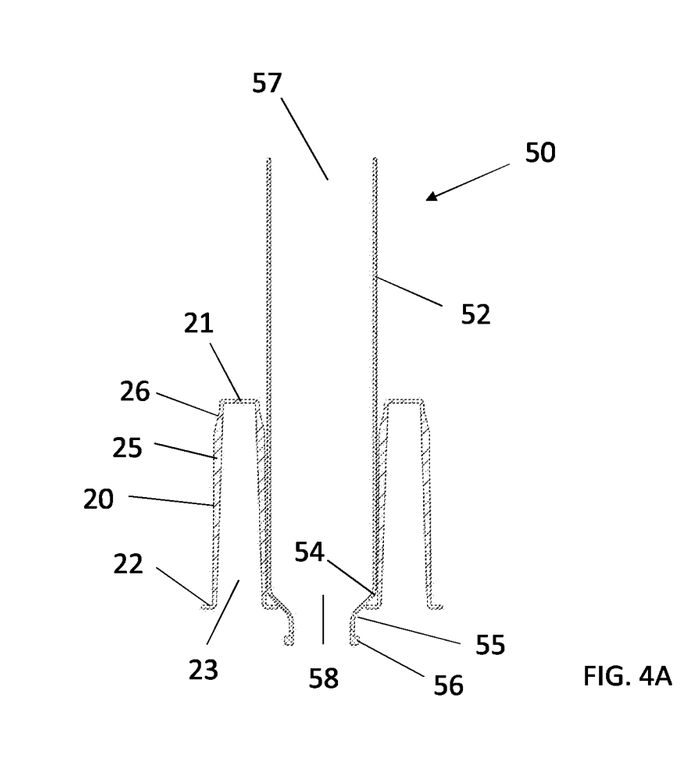
FIG. 4A illustrates a representation of the partial detail according to FIG. 3 with a cartridge accommodated upside down in the receptacle.
Figure 4B:
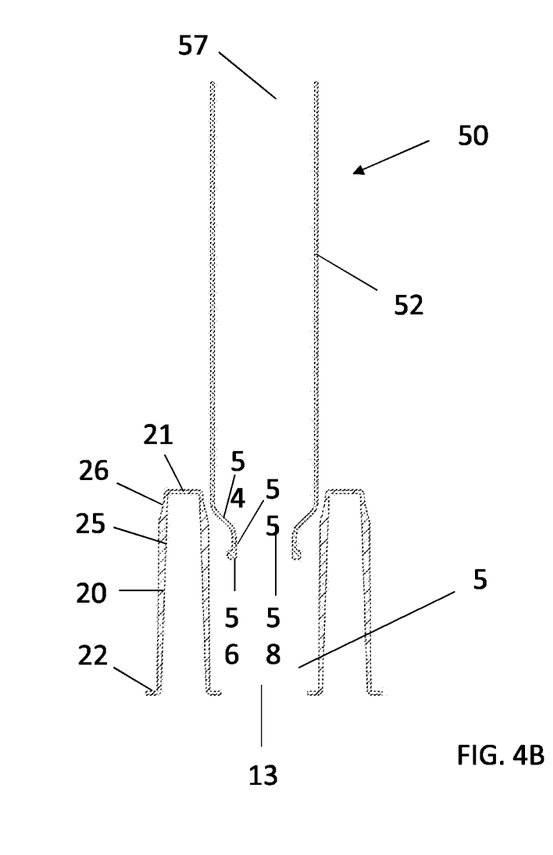
FIG. 4B illustrates a representation of the partial detail according to FIG. 3 at the beginning of the vertical insertion of the cartridge from above into the associated receptacle.

FIGS. 4A and 4B show the insertion of a cartridge 50 from vertical above into the receptacle 5 of a holding structure in two phases, namely in a fully inserted condition (FIG. 4A) and at the beginning of vertical insertion (FIG. 4B). The cartridges 50 are hollow cylindrical, with a cylindrical side wall 52 that merges over an inclined shoulder portion 54 into a constricted neck portion 55 having a smaller outer diameter than the cylindrical side wall 52, at the front end of which a widened rim 56 with an ejection opening 58 is formed. This may be closed by a stopper. The stopper may be secured by a crimped metal cover at the front end of the cartridge 50 (so-called pre-crimped cartridge). At its rear end, the cartridge 50 is open, with a filling opening 57 through which a liquid substance can be filled.

When a cartridge 50 is inserted vertically from above into the receptacle 5, first the front end with the ejection opening 58 enters the region between the upper ends of the positioning cylinders 20 and the side walls. The front end of the cartridge 50 is guided into the receptacle 5 by the lead-in bevels 26 (and 19) provided in this region. As the cartridge 50 continues to approach, the transition region between the shoulder portion 54 and the cylindrical side wall 52 comes into contact with the lead-in bevels 26 (and 19), whereby the front end of the cartridge 50 is guided further into the receptacle 5. As the cartridge 50 continues to approach, the transition region between the shoulder portion 54 and the cylindrical sidewall 52 continues to be guided by the lead-in bevels 26 (and 19) until the transition region between the shoulder portion 54 and the cylindrical sidewall 52 slides along the guiding ribs 25 (and 18) until finally the shoulder portion 54 is directly supported on the holding protrusions 22. In this condition (see FIG. 4A), at least the front end of the cylindrical side wall 52 rests directly on the bottom end of the guiding ribs 25 (and 18) and is thus centered in the receptacle 5 and supported at a distance from the side walls 10 and positioning cylinders 20. In this condition, the front end of the cartridge including the constricted neck portion 55 and the widened upper rim 56 extends through the opening 23 between the holding protrusions 22, possibly including a metal lid crimped onto it. The metal lid does not come into contact with the holding protrusions 22, so that no forces are exerted on them and the stopper can safely close the filling opening 13 of the cartridge 50, even if large axial forces act on the cartridge 50, e.g. when inserting a plunger into the filling opening 57, while the cartridge 50 is accommodated and supported upside-down in the receptacles 5 in the position according to FIG. 4A. In this position, the rear ends of the cartridges 50 protrude from the receptacles 5.

Figure 5A:
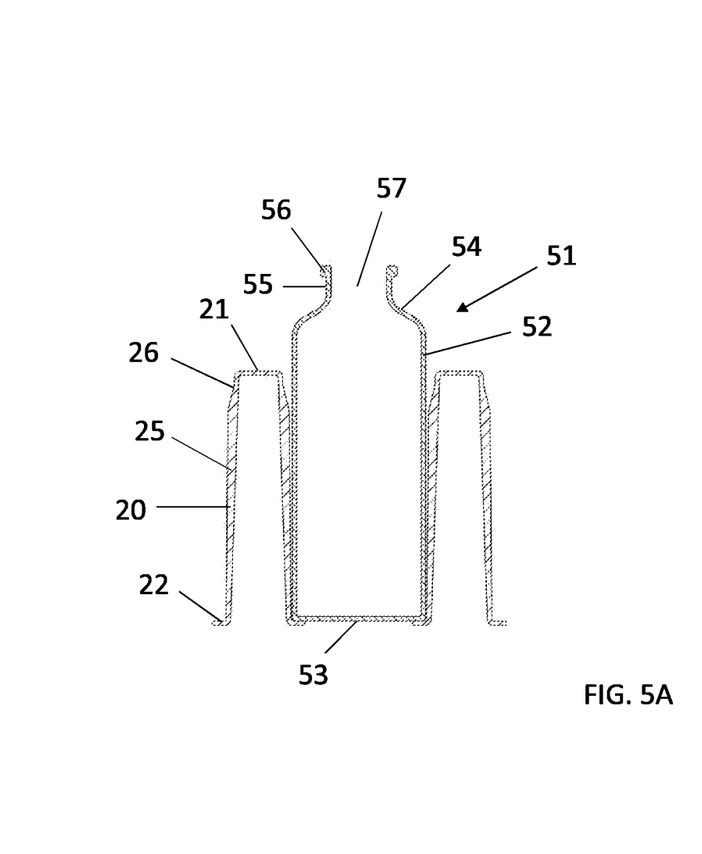
FIG. 5A illustrates a representation of the partial detail according to FIG. 3 with an upright vial accommodated in the receptacle.
Figure 5B:
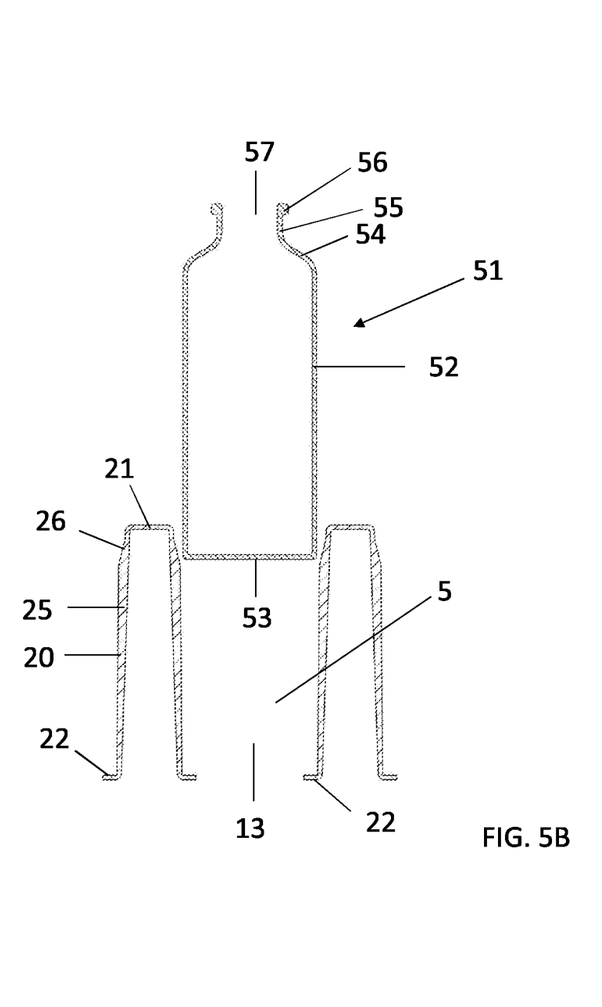
FIG. 5B illustrates a representation of the partial detail according to FIG. 3 at the beginning of the vertical insertion of the vial from above into the associated receptacle.

Accordingly, FIGS. 5A and 5B show the insertion of a vial 51 from vertically above into the receptacle 5 of a holding structure in two phases, namely in a fully inserted condition (FIG. 4A) and at the beginning of insertion (FIG. 4B). It is shown that the vial 51 is inserted upright. Generally, the vial 51 can also be inserted upside-down, as shown in FIGS. 4A and 4B. The guidance of the vial 51 during insertion described above is accomplished by the interaction of the transition region between the bottom 53 and the cylindrical side wall 52 of the vial with the lead-in bevels 26 (and 19) and the guiding ribs 25 (and 18). In the fully inserted state, the bottom 53 of the vial 51 is supported on the holding protrusions 22 and the vial 51 is thus secured in the receptacle 5 in axial direction.

Figure 6:
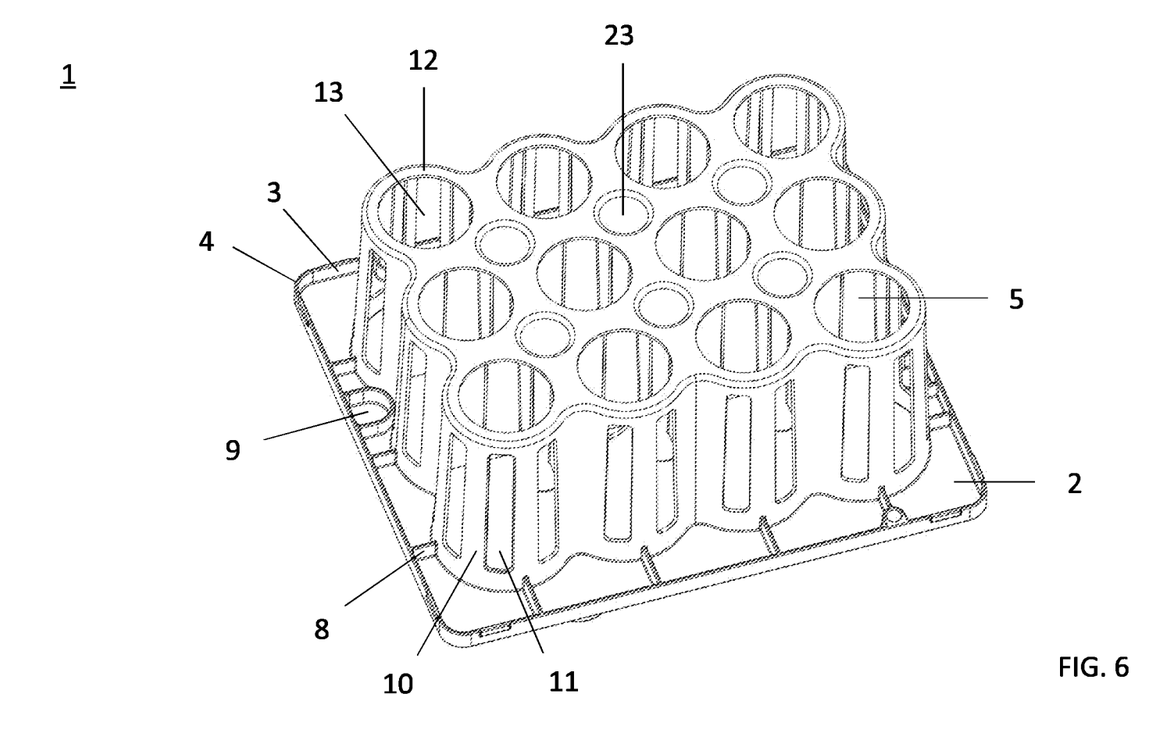
FIG. 6 illustrates the holding structure according to FIG. 1 in a perspective bottom view.
Figure 7:
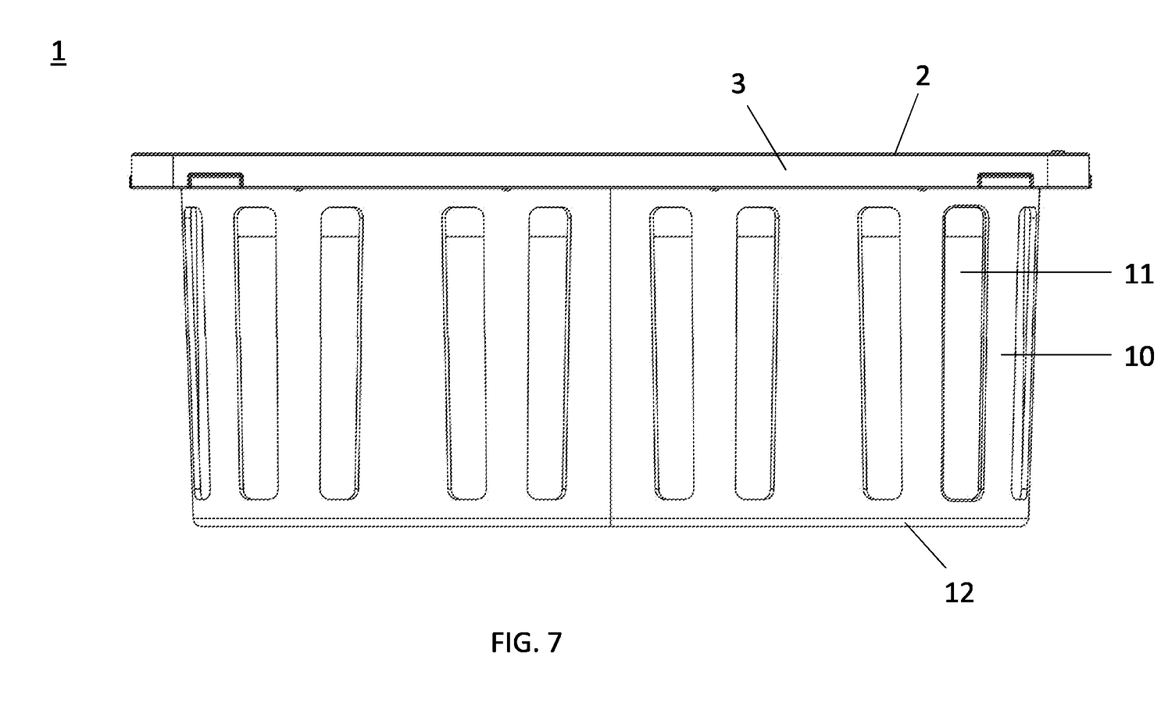
FIG. 7 illustrates the holding structure according to FIG. 1 in a side view.

As shown in FIG. 6, stiffening ribs 8 are provided on the rear side of the holding structure 1 for further stiffening. The cup-shaped design of the receptacles 5 is clearly visible.

A holding structure 1, as described above, can be used for storage and transport of pharmaceutical containers such as vials or cartridges. For handling, the holding structure 1 can be gripped and guided by means of grippers or the like via the access openings 9. The pharmaceutical containers can be further processed or processed while held by the holding structure 1, as described above. For sterile transport, such a holding structure may be stored as a so-called nest in a tub-shaped transport or packaging container, for example in the manner disclosed in European Patent Application EP 2 868 593 A1, the contents of which are hereby incorporated by reference for disclosure purposes. The transport or packaging container may be closed or sealed by a gas-permeable plastic film, in particular by a plastic film which is formed from a gas-permeable braid of plastic fibers and in particular is a TYVECK® film.

Such a holding structure can be formed in one piece, in particular by injection molding from a plastic material. The lead-in bevels and guiding ribs assist the demolding of the holding structure.

Figure 8A:
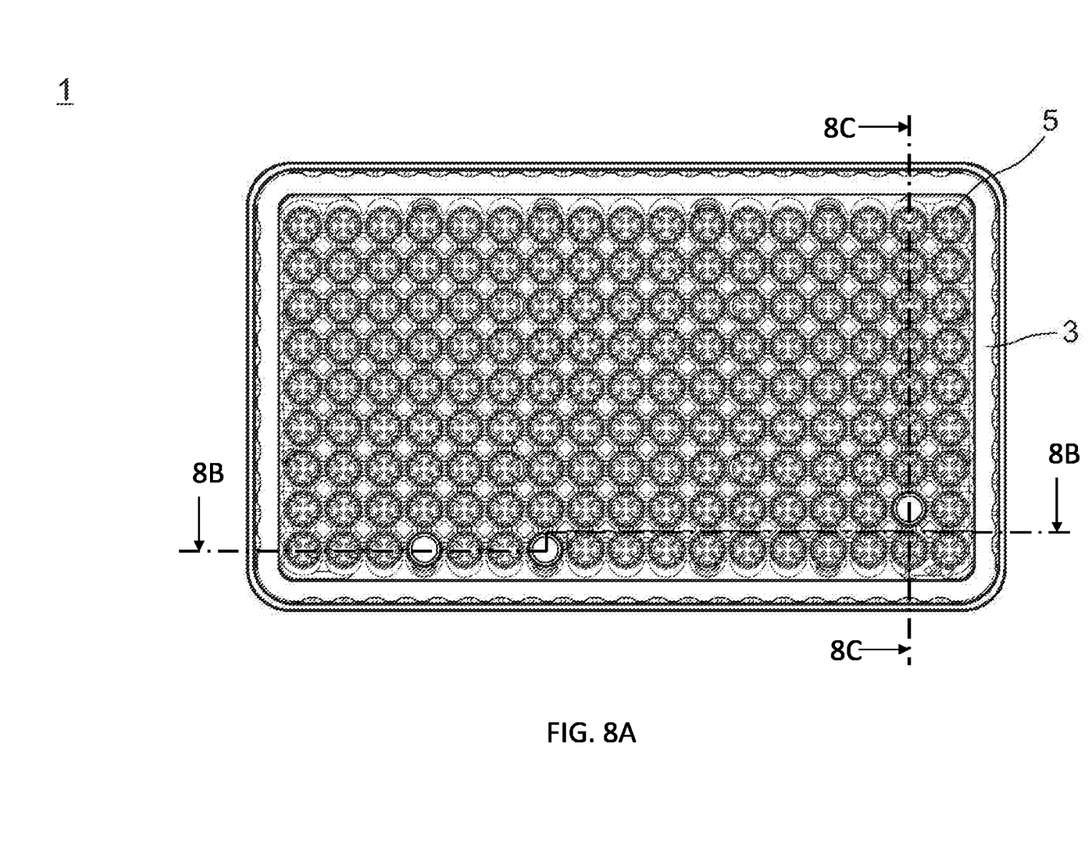
FIG. 8A illustrates a holding structure according to another exemplary embodiment of the present disclosure in a plan view.
Figure 8B:
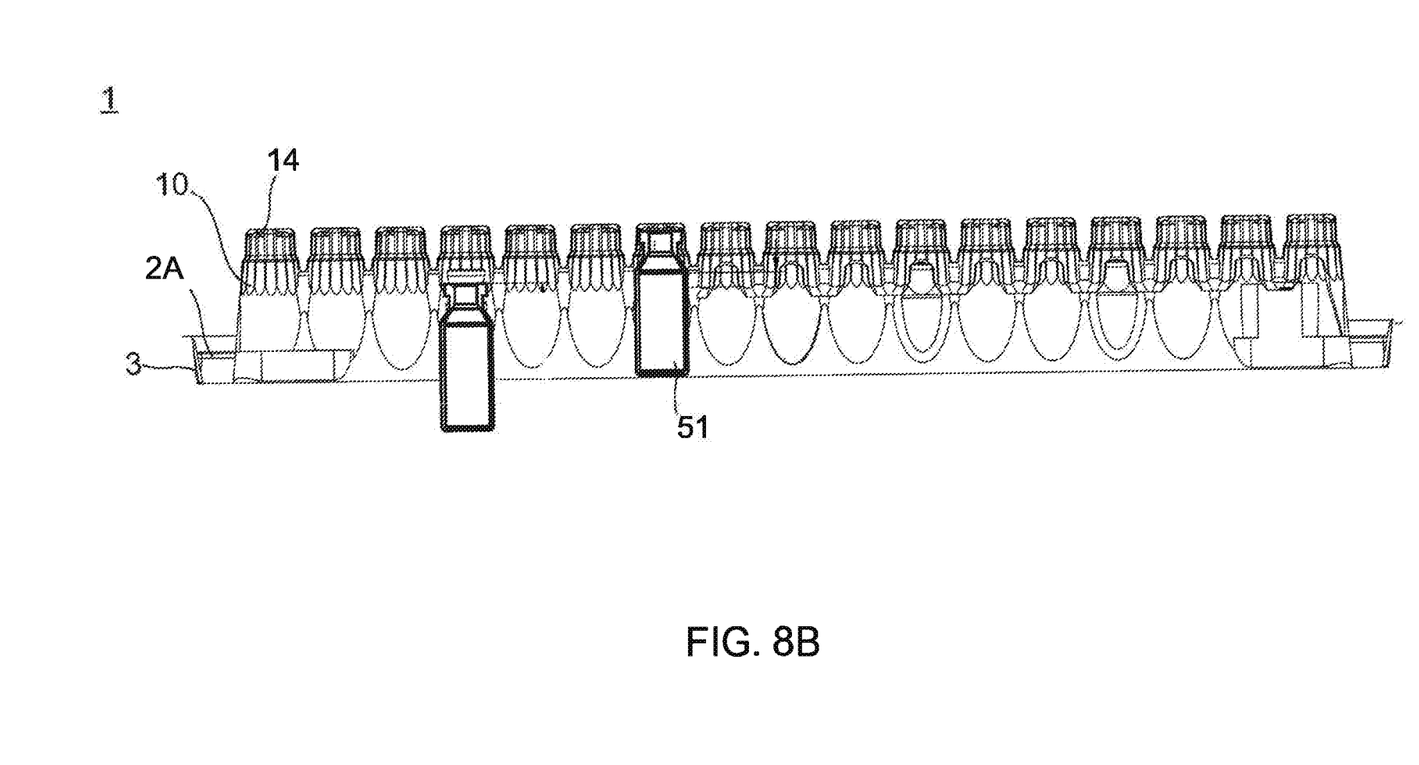
FIG. 8B illustrates a partial section along line 8B-8B in FIG. 8A.
Figure 8C:
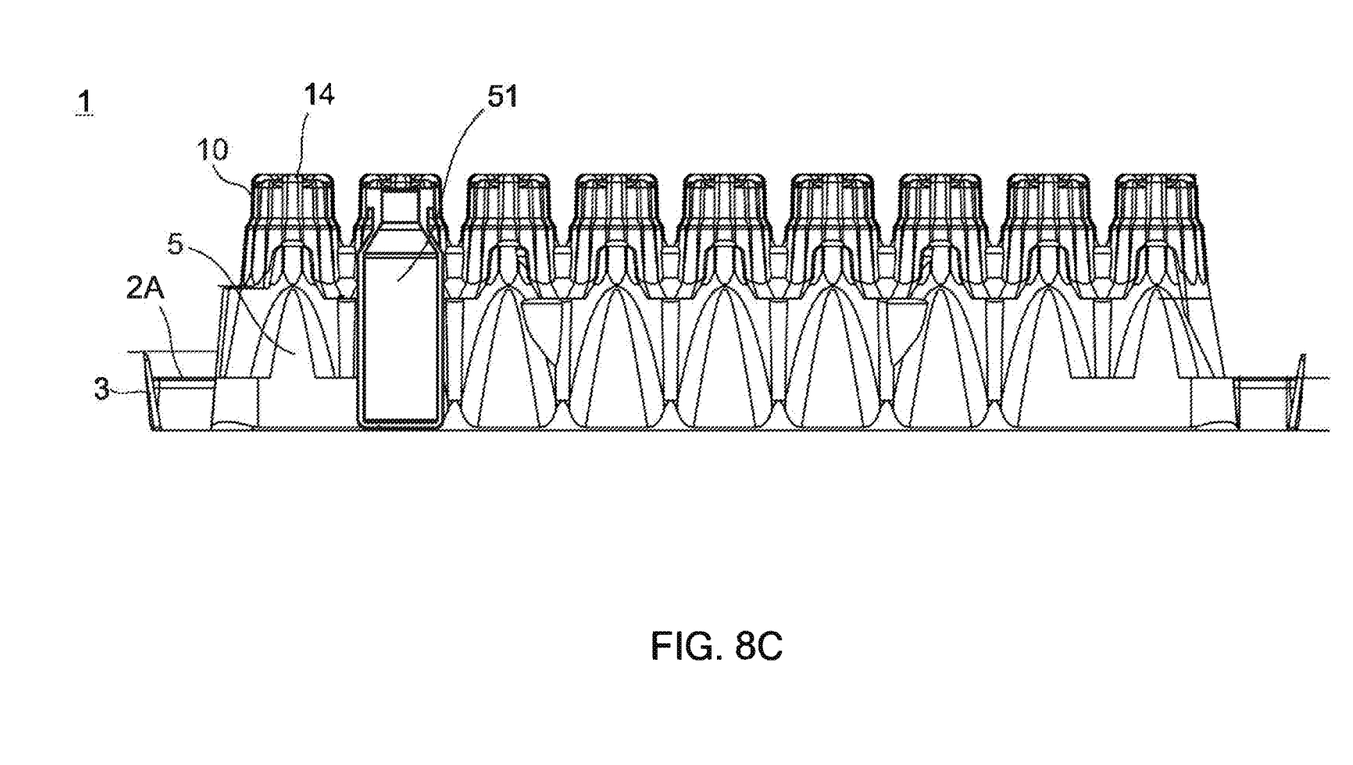
FIG. 8C illustrates a partial section along line 8C-8C in FIG. 8A.

A holding structure provided according to the present disclosure is, however, basically also suitable for so-called tray solutions, especially for vials, as shown in FIGS. 8A to 8C.

According to FIGS. 8A to 8C, the holding structure 1 is designed as a receiving member, in which the majority of the receptacles are formed in one piece and in a regular arrangement as frustoconical receptacles 5. The receptacles 5 are closed by circumferential side walls 10. The vials 51 (as an example of a pharmaceutical container) are directed with their upper ends towards the bottoms 14 of the receptacles 5 and are accommodated in the receptacles 5 of the receiving member 1, preventing direct contact between adjacent vials 51. The vials 51 are fully accommodated in the receptacles 5, so that they do not protrude beyond the edge of the holding structure 1. The lengths of the receptacles 5 may be matched to the vials 51 so that the bottoms of the vials 51 are flush with the edge of the holding structure 1. The lead-in bevels and guiding ribs described above are formed on the inner side of the side walls 10.

To form a transport structure, additionally a support member can be placed on the receiving member and connected to it in such a way that the bottoms of the vials accommodated in the receiving member are covered. The support member may be formed by a base plate having a planar support surface facing the receptacles and on which the bottoms of the vials 51 are directly supported.

The receiving member and/or support member of such a holding structure may be formed in one piece by thermoforming a plastic material, in particular by deep-drawing from a plate-shaped plastic material, such as by deep-drawing a thin film or a thin film plate with a material thickness of up to 2.0 mm, such as of up to 1.25 mm or of up to 1.0 mm.

For such a tray system, generally the receiving member may also be manufactured from a plastic material by injection molding, whereby the lead-in bevels and guiding ribs can assist the demolding of the receiving member in the manner described above.

If a non-sterile transport of the pharmaceutical containers is sufficient, the receiving member may be formed to a non-sterile closed transport structure by connecting it to the support member. If a sterile transport of the pharmaceutical containers is desired, the open side of the receiving member may also be sealed with a sealing film, for example by bonding along a flange-like edge of the receiving member, if necessary with additional welding points, to form a sterile transport structure.

For sterile transport, such a transport structure may be accommodated in at least one sterile outer packaging bag, possibly together with other similar transport structures, and packed sterile against the environment. The at least one sterile outer packaging bag may have a gas-permeable portion or even be completely formed by it, which is formed in particular by a braid of plastic fibers, such as polypropylene fibers (PP).

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS 1 holding structure
2 upper side
2A bottom
3 upper edge
4 rounded corner region
5 receptacle
5A inner receptacle
5B outer receptacle
6 upper edge
7 rounded edge region
8 stiffening rib
9 access opening
10 side wall
11 slot
12 bottom web
13 opening
14 bottom
15 separation webs
16 rib
18 guiding rib
19 lead-in bevel of guiding rib 18
20 positioning pin
21 upper end of positioning pin 20
22 holding protrusion
23 cavity
24 upper edge region
25 guiding rib
26 lead-in bevel of guiding rib 25
27 rounded edge region
50 cartridge/container
51 vial/container
52 side wall
53 bottom
54 shoulder portion
55 narrowed neck portion
56 upper edge
57 filling opening
58 ejection opening

What is claimed is:

1. A holding structure for concurrently holding a plurality of containers for substances for pharmaceutical, medical or cosmetic applications, the holding structure comprising:
a plurality of receptacles for receiving the containers therein at least in sections, the receptacles each having an open upper end for inserting the containers into the receptacles and a bottom end having a holding portion configured to limit an axial movement of the containers in the receptacles;
guide portions provided and configured to guide the containers as they are inserted into the receptacles, the guide portions being formed as guiding ribs extending in a longitudinal direction of the receptacles, each of the guiding ribs being inclined at an angle of inclination relative to a central axis of a respective one of the receptacles, the angle of inclination being larger than 0° and less than or equal to 2°; and
lead-in bevels formed at upper ends of the guiding ribs which are inclined relative to the guiding ribs, wherein the lead-in bevels are inclined relative to the guiding ribs at an angle in the range between 5° and 15°.

2. The holding structure of claim 1, wherein the angle of inclination is larger than 0° and less than or equal to 1.5°.

3. The holding structure of claim 2, wherein the angle of inclination is larger than 0.5° and less than or equal to 1.0°.

4. The holding structure of claim 1, wherein the lead-in bevels are inclined relative to the guiding ribs at an angle in the range between 10° and 15°.

5. The holding structure of claim 4, wherein the lead-in bevels are inclined relative to the guiding ribs at an angle in the range between 12.5° and 14.5°.

6. The holding structure of claim 1, wherein the guiding ribs protrude radially inwards into the receptacles and are arranged distributed at angular spacings from one another.

7. The holding structure of claim 1, wherein the guiding ribs of a respective receptacle surround a circle of a diameter that is smaller than a diameter of the respective receptacle, wherein the diameter of the circle at bottom ends of the guiding ribs corresponds to an outer diameter of a respectively received container.

8. The holding structure of claim 1, wherein inner receptacles of the holding structure are formed by positioning cylinders extending in an axial direction, on side walls of which a plurality of guiding ribs are provided.

9. The holding structure of claim 8, wherein the guiding ribs of diametrically opposite positioning cylinders of a respective inner receptacle are arranged in alignment, and wherein the guiding ribs are arranged on the side walls of the positioning cylinders at angular spacings of 90° relative to each other.

10. The holding structure of claim 8, wherein the positioning cylinders are connected to each other via separation webs which are aligned along rows and columns.

11. The holding structure of claim 9, wherein the positioning cylinders are hollow cylindrical in shape, wherein an upper side edge of the positioning cylinders is rounded.

12. The holding structure of claim 1, wherein outer receptacles of the holding structure are formed by side walls which are curved in a circular manner at least in sections, an upper edge of the side walls being rounded.

13. The holding structure of claim 1, wherein the holding portions are formed as holding protrusions protruding radially inwards, the holding protrusions surrounding respective openings at the bottom ends of the receptacles.

14. The holding structure of claim 1, wherein an upper side of the holding structure is planar at least along an edge of the holding structure and the bottom ends of the receptacles are connected to one another via webs which jointly span a plane.

15. The holding structure of claim 14, wherein the holding structure is formed as a nest for receiving the plurality of containers therein.

16. The holding structure of claim 1, wherein a length of each receptacle is matched to a length of a respective one of the containers such that upper ends or bottom ends of each container protrude from its respective receptacle and are freely accessible from above the holding structure.

17. The holding structure of claim 1, wherein the holding structure is integrally formed from a plastic material by injection molding.

18. The holding structure of claim 1, wherein the holding structure is formed as a receiving member in which the plurality of receptacles are integrally formed as frustoconical receptacles in a regular arrangement, so that the containers are directed with their upper ends towards the bottoms of the receptacles and can be accommodated in the receptacles of the receiving member while preventing direct contact of adjacent containers, and the receptacles are matched to the lengths of the containers so as to accommodate the containers therein completely;

said holding structure further comprising a support member for covering bottoms of the containers accommodated in the receiving member, the support member being formed by a base plate having a planar support surface facing the receptacles.

19. The holding structure of claim 18, wherein the receiving member is formed in one piece by thermoforming a plastic material by deep-drawing from a plate-shaped plastic material.

20. A transport structure, consisting of a combination of:
a holding structure for concurrently holding a plurality of containers for substances for pharmaceutical, medical or cosmetic applications and a plurality of containers held thereon, the holding structure comprising:
   a plurality of receptacles for receiving the containers therein at least in sections, the receptacles each having an open upper end for inserting the containers into the receptacles and a bottom end having a holding portion configured to limit an axial movement of the containers in the receptacles, the containers being accommodated in the receptacles at least in sections and are held axially secured to the holding structure;
guide portions provided and configured to guide the containers as they are inserted into the receptacles, the guide portions being formed as guiding ribs extending in a longitudinal direction of the receptacles, each of the guiding ribs being inclined at an angle of inclination relative to a central axis of a respective one of the receptacles, and the angle of inclination being larger than 0° and less than or equal to 2°; and
lead-in bevels are formed at upper ends of the guiding ribs which are inclined relative to the guiding ribs, wherein the lead-in bevels are inclined relative to the guiding ribs at an angle in the range between 5° and 15°.

\* \* \* \* \*